United States Patent [19]

Rousseau

[11] Patent Number: 4,749,020

[45] Date of Patent: Jun. 7, 1988

[54] APPARATUS FOR OBTAINING IMPROVED DENTAL CASTINGS

[76] Inventor: Carl H. Rousseau, 1510 Barry St., Clearwater, Fla. 33516

[21] Appl. No.: 893,217

[22] Filed: Aug. 4, 1986

Related U.S. Application Data

[63] Continuation-in-part of Ser. No. 718,178, Apr. 1, 1985, Pat. No. 4,603,728, which is a continuation-in-part of Ser. No. 385,025, Jun. 4, 1982, Pat. No. 4,508,155.

[51] Int. Cl.$^4$ .................. B22C 7/02; B22C 9/04; B22C 21/00
[52] U.S. Cl. .................. 164/237; 164/244; 164/376; 164/377; 249/54
[58] Field of Search .............. 164/237, 244, 376, 377; 249/54

[56] References Cited

U.S. PATENT DOCUMENTS

| 1,970,261 | 8/1934 | Turner | 164/376 |
| 2,193,357 | 3/1940 | Greth | 164/376 |
| 2,267,329 | 12/1941 | Fowler et al. | 164/376 |

FOREIGN PATENT DOCUMENTS

| 597491 | 2/1978 | U.S.S.R. | 164/376 |

Primary Examiner—Nicholas P. Godici
Assistant Examiner—J. Reed Batten, Jr.
Attorney, Agent, or Firm—Frijouf, Rust & Pyle

[57] ABSTRACT

An apparatus for the preparation of a dental casting from a dental pattern utilizing an exothermic investment material which expands upon curing which comprises a base having a top surface for supporting the dental pattern and a container having a first and a second open end. The container and the base partially enclose the dental pattern when the first open end of the container is disposed upon the top surface of the base. The second end of the container enables the introduction of the exothermic investment material to compeletly encompass the dental pattern. The container comprises a first and a second container portion with each of the first and second container portions having a first and a sonnd terminating edge. The first and second terminating edges of the first container portion respectively cooperate with the second and first terminating edges of the seocnd container portion for retaining the uncured exothermic investment material within the container. The first and second terminating edges of the first container portion separate from the second and first terminating edges of the second container portion during the expansion of the exothermic investment material upon the exothermic reaction thereof for producing improved accuracy in the dental casting.

23 Claims, 4 Drawing Sheets

APPARATUS FOR OBTAINING IMPROVED DENTAL CASTINGS

CROSS-REFERENCE TO RELATED APPLICATIONS

This application is a continuation-in-part of pending application Ser. No. 718,178, filed Apr. 1, 1985 now U.S. Pat. No. 4,603,728. Application Ser. No. 718,178, filed Apr. 1, 1985 is a continuation-in-part of application Ser. No. 385,025, filed June 4, 1982, now U.S. Pat. No. 4,508,155. All matter set forth in application Ser. No. 718,178 and application Ser. No. 385,025 is hereby incorporated by reference.

BACKGROUND OF THE INVENTION

1. Field of the Invention

The present invention relates to an apparatus and method useful for obtaining improved dental castings according to the lost wax method. The apparatus and method of this invention permit dental castings of extreme accuracy to be prepared using base metal alloys rather than precious metals such as gold and the like.

2. Description of the Prior Art

Various techniques and forms of apparatus are old and well known for preparing castings according to the lost wax method. Use of the lost wax method within the dental profession for the purpose of casting crowns and other such dental restorations is similarly well known. Of particular note with regard to dental castings is the fact that dental castings require extreme accuracy in the final product. Accordingly, metallurgical characteristics have virtually dictated that the castings be prepared from precious metals such as gold and the like. Numerous attempts have been made to prepare dental castings from base metal alloys but heretofore base metal castings generally required excessive finish work so that the restoration will fit properly.

Yet another problem inherently present in all casting techniques utilizing the lost wax method is the fact that curing of the investment material is an exothermic reaction. In an exothermic reactions, the investment material generates heat as the investment material hardens or cures. This necessarily results in "swelling" of the investment material, and the swelling usually results in at least some compression of the wax model within the investment. The compression against the wax model for a dental restoration will have an undesirable effect of distorting the restoration pattern. When the pattern is burned out and a molten metal is cast into the void formed within the hardened investment material, the casting will not correspond exactly to the original pattern. This results not only in discomfort to the patient, but unnecessary expenditure of time, energy and money for the patient, the dentist, and the dental technician.

Insofar as the problem of obtaining accurate castings utilizing base metal alloys is concerned, the only effective solution available today involves either detailed and expensive hand-finishing of the casting, the taking of new impressions and making new castings, or simply accepting a relatively inferior final product. Another solution to this problem would be to prepare all castings from gold rather than a base metal alloy, but this obviously has an adverse economic impact on the patient.

U.S. Pat. No. 2,337,036 to Erdle discloses the use of a resilient mold for making porcelain dental restorations. While analogous to the field of preparing dental restorations, the resilient mold of U.S. Pat. No. 2,337,036 would not appear to be suitable for metal castings according to the lost wax process. U.S. Pat. No. 2,243,445 discloses an expansible absorbent receptacle for investments. U.S. Pat. No. 2,450,567 to Schwartz discloses a two-part flask for retaining investment material. Yet another casting ring constructed and arranged to prevent breakage of an investment made therein is disclosed in U.S. Pat. No. 1,976,655 to Carpenter.

While these patents disclose apparatus including investment ring constructions, none of these prior art teachings make any attempt to solve the problem created by the fact that as the exothermic reaction takes place before solidification of the investment material. As the wax pattern is subsequently burned out from within the investment material, different areas within the volume defined by the investment experience different temperatures.

In my prior invention filed as patent application Ser. No. 385,025 filed June 4, 1982, I disclosed an apparatus and a method for making improved full arch dental implants utilizing a unitary expandable investment ring in combination with a base and novel a sprue former and runner bar means. My prior invention as disclosed in application Ser. No. 385,025 solved many of the problems heretofore described and was issued U.S. Pat. No. 4,508,155.

In a further improvement upon my prior invention, I disclosed in application Ser. No. 718,178 filed Apr. 1, 1985 an improvement to the runner bar means which allowed even greater accuracy in full arch dental implants. The present application further improves upon the investment ring or container means set forth in my prior patent application Ser. Nos. 385,025 and 718,178.

The foregoing has outlined some of the more pertinent objects of the present invention. These objects should be construed to be merely illustrative of some of the more pertinent features and applications of the invention. Many other beneficial results can be obtained by applying the disclosed invention is a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The present invention relates to apparatus and a method for obtaining improved dental castings according to the lost wax method, and is especially suited for preparing castings from base metal alloys such as, for example, nickel-chromium-beryllium alloys. However, it is to be understood that the apparatus and method of the present invention is also suitable for use in preparing precious metal castings. By virtue of the apparatus and method of the present invention, a metal casting is repeatedly obtainable that will withstand examination under a 25 power stereoscopic microscope and demonstrate virtually absolute integrity of the marginal area. For example, base metal castings prepared utilizing the apparatus and method of the present invention exhibit size variance of less than 10 microns, while the current state of the art in casting dental restorations accepts variance as great as 100 microns.

The invention is incorporated into a method and an apparatus for the preparation of a dental casting from a dental pattern supported by a sprue utilizing an exothermic investment material which expands upon curing. The apparatus comprises a base means having a top surface for supporting the sprue and the dental pattern and includes container means having a first and a second open end. The container means and the base means partially enclose the sprue and the dental pattern when the first open end of the container means is disposed upon the top surface of the base means. The second end of the container means enables the introduction of the exothermic investment material to completely encompass the sprue and the dental pattern. The container means comprises a first and a second container portion with each of the first and second container portions having a first and a second terminating edge. The first and second terminating edges of the first container portion respectively cooperates with the second and first terminating edges of the second container portion for retaining the uncured exothermic investment material within the container means. The first and second terminating edges of the first container portion separates from the second and first terminating edges of the second container portion during the expansion of the exothermic investment material upon the exothermic reaction thereof.

In one embodiment of the invention, the first and second terminating edges of the first and second container portions extend generally normal to the top surface of the base means when the first open end of the container means is disposed upon the top surface of the base means. Preferably, the first and second terminating edges of the first and second container portions have portions thereof which extend angularly relative to the normal to the top surface of the base means when the first open end of the container means is disposed upon the top surface of the base means.

The first and second container portions of the container means may be designed such that the first and second container portions are identical. Accordingly, the second container portion may be inverted relative to the first container portion for enabling the first and second terminating edges of the first container portion to respectively cooperate with the second and first terminating edges of the second container portion.

In another embodiment of the invention, the first terminating edges of the first and second container portions are undercut on an outer surface of the first and second container portions, respectively. Similarly, the second terminating edges of the first and second container portions are undercut on an inner surface of the first and second container portions for enabling cooperation between the undercuts on the outer and the inner surfaces.

Preferably, means are provided for releasably securing the first container portion relative to the second container portion. In one example, the means for releasably securing the first container portion relative to the second container portion includes a tab secured adjacent to the first edge of the first container portion and an aperture disposed adjacent the second edge of the second container portion for receiving the tab within the aperture. The tab may be tapered for facilitating insertion into the aperture. In addition, the aperture may be internally tapered for insuring proper alignment between the first and second container portions.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

Figures 1, 2, 3, 4, 5, 6, 7, 8, 9:
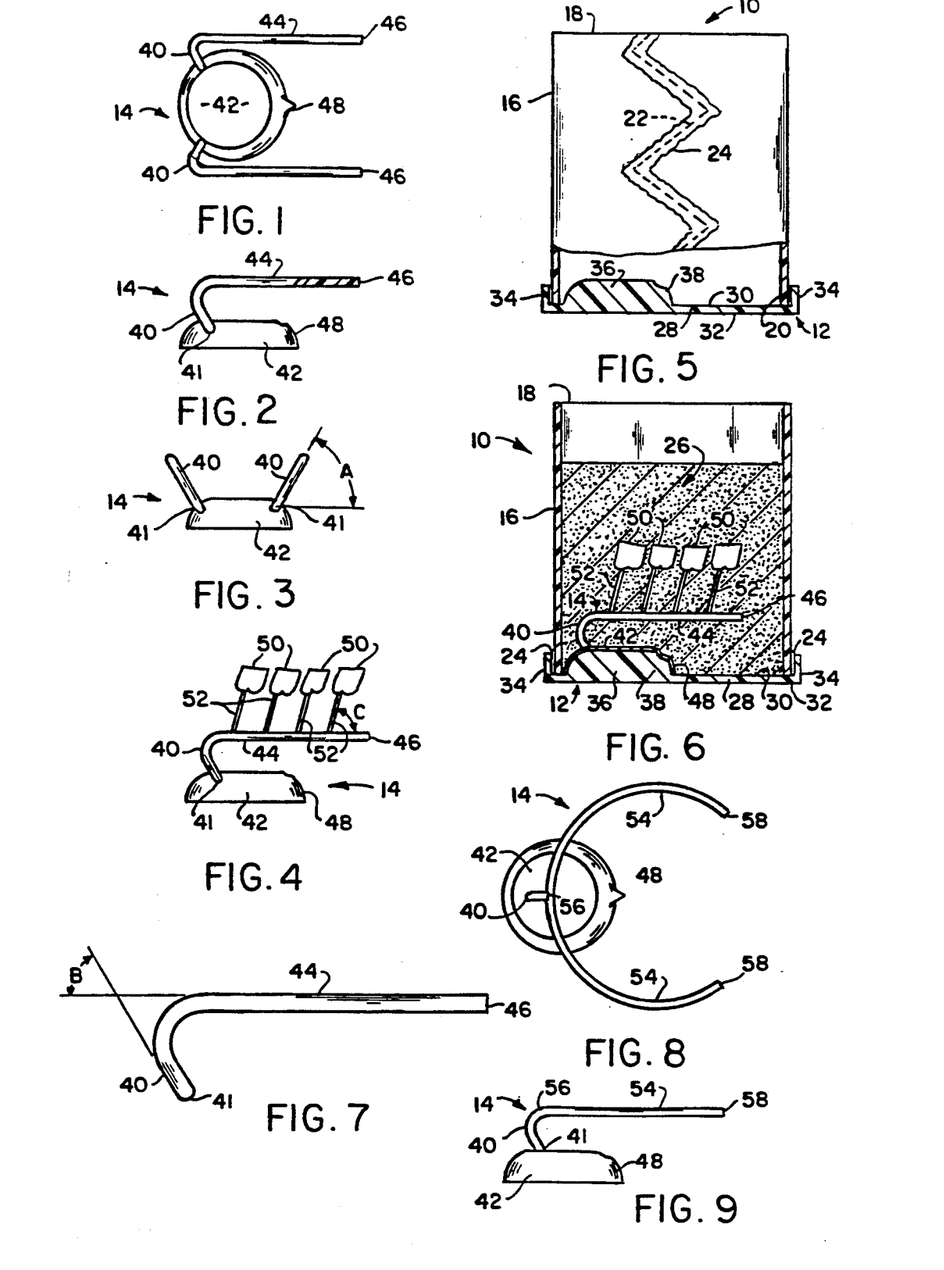
FIG. 1 is a plan view of one embodiment of runner bar means of the present apparatus.
FIG. 2 is a side view of the runner bar means shown in FIG. 1.
FIG. 3 is an end view of the runner bar means shown in FIG. 1.
FIG. 4 is a side view similar to FIG. 2 illustrating the attachment of wax patterns by sprue segments to the runner bar means.
FIG. 5 is a side view partially in section illustrating the investment ring or container means mounted on a base means.
FIG. 6 is a side sectional view of the apparatus after the investment material has been poured.
FIG. 7 is an enlarged detailed view of a curved proximal end and elongate bar of the runner bar means.
FIG. 8 is a plan view similar to FIG. 1 illustrating a second embodiment for the runner bar means.
FIG. 9 is a side view of the runner bar means shown in FIG. 8.

As perhaps most clearly seen in the views of FIGS. 1 and 5, the apparatus for obtaining improved dental castings comprises an investment container or ring generally indicated as 10, base means generally indicated as 12, and runner bar means generally indicated as 14. Considering first the investment ring 10, and with regard to the views of FIGS. 5 and 6, it can be seen that ring 10 is defined by a substantially columnar tube 16 having a second open end 18 a first open end 20 thereof. A fracture, or seam, 22 extends along the longitudinal dimension of tube 16 from open end 18 to open end 20. As seen in the view of FIG. 5, fracture 22 is preferably formed along a zig-zag path. Fracture 22 is shown in phantom in the view of FIG. 5 for the reason that this figure illustrates the applications of heat sealing means shown as vax 24 over the outside of tube 16 along fracture 22 for sealing purposes prior to pouring the investment material (not shown in FIG. 5, but designated 26 in the view of FIG. 6).

The investment container may also be made of a tubular expandable material which is characterized by the ability to expand in all directions under the heat and pressure conditions created by the curing of the investment material and also be thermal resistant at the investment material curing temperature. This container would alleviate the need for fracture 22 since the entire container 10 would expand. Any elastomer, for example natural or a synthetic rubber such as butyl rubber, or a resilient polymer such as polypropylene, which meets the above criteria and can be shaped into a tubular container is within the scope of this invention.

Base means 12 comprises a substantially circular plate 28 having a top surface 30 and a bottom surface 32. A lip 34 is formed around the perimeter of plate 28 and extends upwardly from top surface 30 in substantially perpendicular relation thereto. As clearly seen in the view of FIG. 5, the inside diameter of base means 12 is greater than the outside diameter of tube 16 so that the investment ring 10 may be disposed within the base means 12.

Base means 12 further comprises a sprue former 36 integrally formed on top surface 30, and sprue former 36 includes an index tip 38 formed thereon. The function of sprue former 36 and index tip 38 will be described in greater detail hereinafter.

Finally, the runner bar means 14 is most clearly illustrated in the views of FIGS. 1-4, inclusive. As best seen in the view of FIG. 2, runner bar means 14 comprises a curved proximal end portion 40 having a proximal end 41 connected to a coping 42, and a distal end portion 44 extending from curved proximal end portion 40 and terminating in a distal end 46. Coping 42 further comprises an indexed receiver 48 formed thereon whereby the runner bar means 14 may be operatively disposed over sprue former 36 of base means 12 with the index receiver 48 an mating relation to index tip 38. Of course, as is clearly illustrated in the views of FIGS. 1 and 3, the runner bar means of this invention comprises a corresponding pair of curved proximal ends 40, distal end portions 44, and distal ends 46. It is to be understood that there is no intention of limiting the scope of the present invention to such a paired construction. The runner bar means 14 may certainly comprise a single curved proximal end portion 40, distal end portion 44, and distal end 46. In such an embodiment it is contemplated that curved proximal end 40 would be connected to coping 42 such that distal end portion 44 would substantially bisect the top of coping 42 when viewed in top plan similar to that of FIG. 1.

Inasmuch as this preferred embodiment does, however, comprise a paired construction, attention is invited to the view of FIG. 3 wherein the relative disposition of the two curved proximal end portion 40 with respect to the plane defined by the top of coping 42 may be seen. This angular relationship has been indicated by arrows A and preferably is about 60°. By virtue of this construction, wax patterns 50, and the voids created thereby according to lost wax methods, are positioned within investment material 26 so as to minimize adverse effects of heating, cooling compression, and expansion.

Also of special note, and as best seen in the view of FIG. 7, the curvature of proximal end portion 40 defines an angle of about 55°-65° with respect to distal end portion 44. Angle B in the view of FIG. 7 identifies this angular relationship which is preferably about 57°. As already stated, above, this angular relationship between proximal end portion 40 and distal end portion 44 serves to control and regulate the flow of molten alloy into the mold cavity to insure base metal alloy castings of extremely high accuracy. Accordingly, this angular relationship B is present in all embodiments of the apparatus of this invention.

Attention is now invited to the view of FIG. 4 wherein the means for attaching wax patterns 50 to distal end portion 44 is illustrated. While the physical means for attachment is quite standard and comprises segments 52 of sprue wax, the relative position of segments 52 with respect to distal end 46 is quite important to the efficacy of this apparatus. The angular relationship between segments 52 and distal end 46 is designated by angle C in the vie of FIG. 4 and falls within the range of about 50°-90°. Preferably, this angle is about 75°. Again, as previously stated, angular relationship C is important for the purpose of controlling and regulating the flow of molten alloy into the cavities formed upon burning out wax patterns 50.

The sectional view of FIG. 6 illustrates the preferred embodiment of the apparatus of this invention in operative array. Once wax patterns 50 have been formed they are attached to elongate bar 44 as previously described by sprue segments 52. The entire runner bar means 14 is then operatively disposed on sprue former 36 so that index receiver 48 and index tip 38 are in registry. Appropriate quantities of wax 24 may be utilized as the means for attaching coping 42 in position on sprue former 36. Next, investment ring 10 is mounted on base means 12, fracture 22 is closed by the application quantities of wax 24. As the investment material hardens and releases heat, the entire ring or container means may expand. Just as the investment ring seam is sealed with wax prior to pouring, so is the entire perimeter seam between the investment ring and the base means. Next, previously prepared investment material is poured into the cavity defined by tube 16 and plate 28 to a depth of about 5 mm (one quarter inch) above wax patterns 50. Standard procedures are utilized during the addition of investment material 26 to insure complete filling of the cavity. After the filled apparatus has been allowed to set for about 1 hour, expansion of the investment ring along fracture 22 may be observed. Wax 24, both along fracture 22 and adjacent lip 34 will yield to permit such expansion, thereby virtually eliminating adverse compression forces on wax patterns 50. At this point invention ring 10 and base means 12 may be removed for final preparation of the casting mold according to standard lost wax techniques.

The views of FIGS. 8 and 9 illustrate another embodiment for runner bar means 14. In this embodiment those elements corresponding to the embodiment of FIG. 1 which are identical thereto have been identified by corresponding reference numerals. The significant distinction between the embodiment of FIGS. 8 and 9 and that of FIG. 1 resides in the construction of elongate curved bar 54. As clearly seen in the view of FIG.

8, elongate curved bar 54 is integrally formed on curved proximal end 40 as at midpoint 56 and terminates in a pair of oppositely disposed distal ends 58. This embodiment for runner bar means 14 would be utilized in combination with investment ring 10 and base means 12 substantially as described above, and is particularly useful for dental casting a full arch.

Figures 10, 11:
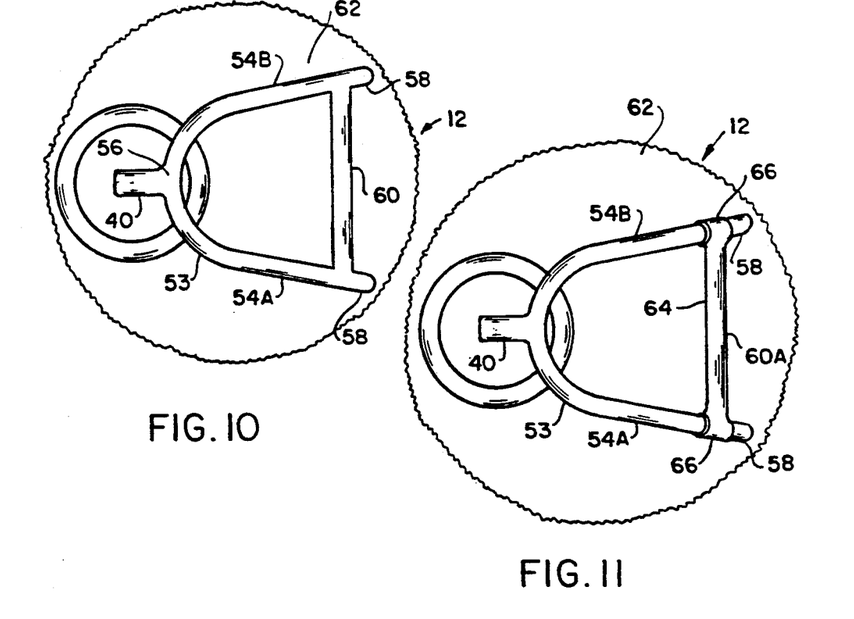
FIG. 10 is a partial plan view of the runner bar means with interconnecting cross-bar means.
FIG. 11 is a partial plan view of the runner bar means with attachable interconnecting cross-bar means.

FIG. 10 illustrates an embodiment for full arch runner bar means 62 connected at the distal ends 58 by interconnecting means 60. As is evident in FIG. 10, an expandable container means 10 (not shown) having a base means 12 with a sprue former 36 (not shown) operatively disposed thereon with a full arch runner bar means 62 operatively disposed on sprue former 36 (not shown) comprising a proximal end portion 40 and a distal end portion 53 with said proximal end portion 40 forming an angle with respect to the distal end portion. The distal end portion 53 forming a first 54A and second 54B curved configuration portion which together approximate the curved configuration of a jawbone of a patient, with interconnecting means 60 integrally formed between the first 54A and second 54B curved configuration portion of distal end portion 53.

FIG. 11 illustrates an embodiment for the full arch runner bar means 62 connecting the first 54A and second 54B curved configuration portion of distal end portion 53 by attachable interconnecting means 60A. Attachable interconnecting means 60A is preferably held in place by a heat resistant adhesive such as a cyanoacrylate ester adhesive in order to stabilize the distal end portion during the investment process. As is evident in FIG. 11, distal end portion 53 is integrally formed on curved proximal end 40 as at mid point 56 with the distal end portion 53 of full arch runner bar forming a first 54A and second 54B curved configuration portion which together approximates the curved configuration of the jawbone of the patient, with attachable interconnecting means 60A linking the first 54A and second 54B curved configuration portion of distal end portion 53.

Figures 12, 13:
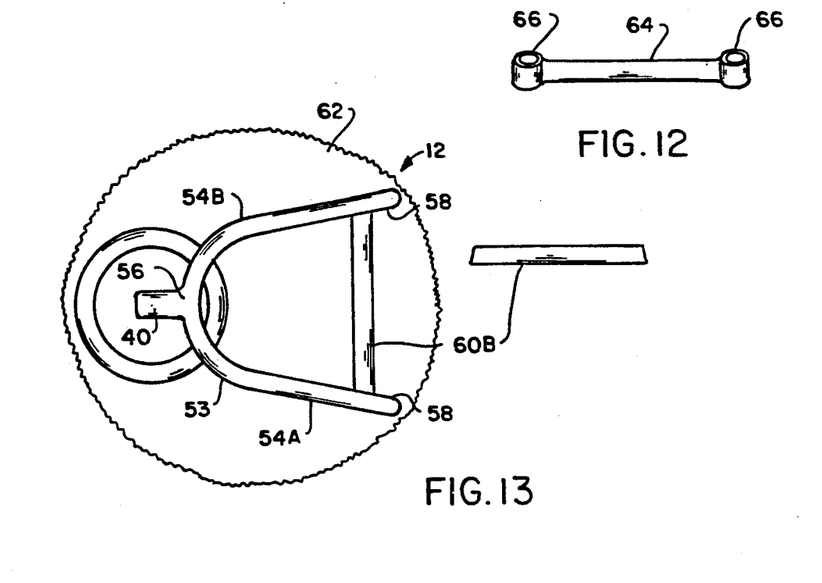
FIG. 12 is a detailed view of the attachable interconnecting cross-bar means shown in FIG. 11.
FIG. 13 is a detailed view of a chemically attachable interconnecting cross-bar means.

FIG. 12 illustrates the attachable interconnecting means 60A which comprises an elongate bar 64 and attachment means 66. The length of the elongate bar is sufficient to interconnect or link the first 54A and second 54B curved configuration portion of distal end portion 53 without distorting distal end portion 53 which approximates the curved configuration of the jawbone of a patient. The attaching means 66 has an inside diameter which is the same as, or slightly greater, than the outside diameter of distal end portions 53 in order to provide for the attachable interconnecting means 60A to be slidably received on the first 54A and second 54B curved configuration portion of distal end portion 53. Once in place, the attachable interconnecting means 60A is preferably permanently attached by the use of a thermal resistant adhesive such as a cyanoacrylate ester adhesive. This procedure insures that the attachable interconnecting means 60A will remain in position prior to and during the investment process.

The view of FIG. 13 illustrates an interconnecting means 60B which comprises an attachable elongate bar which is attached between the first 54A and second 54B curved configuration portion of distal end portion 53 by a chemical adhesive such as for example a cyanoacrylate ester prior to the investment process.

The linking or interconnecting position of attachment of interconnecting means 60, 60A or 60B along the first 54A and second 54B curved configuration portion of distal end portion 53 is preferably at or near the widest distance (this is considered to be the distal end of first 54A and second 54B curved configuration portions) between the first 54A and second 54B curved configuration portion of distal end portion 53, as illustrated in FIGS. 10-13, in order to provide the maximum stabilization of distal end portion 53 without distorting the full arch configuration of which approximates the curved configuration of the jawbone of a patient. Other means of attaching oppositely disposed distal ends 58 may be used to stabilize distal end portion 53 as long as the full arch configuration which approximates the curved configuration of the jawbone of a patient is not distorted.

Distortion of full arch metallic castings depends on a series of complex phenomena. Besides the distortion caused by handling during fabrication and investing using lost wax casting process, distortion occurs within the ceramic investment. The cured ceramic investment is heated to "burn out" or remove the wax pattern, sprue segments, etc., leaving a cavity for subsequent metal pouring. This mold space is then filled with molten alloy metal which solidifies upon cooling. Apparently, the variance in temperature between the investment material and the non-precious metal and the inherent mismatch between the coefficient of thermal expansion and contraction of the ceramic investment material and metal, results in distortion especially notable with full arch casting. Also, the higher fusion temperature of non-precious metal alloys creates casting shrinkage which further adds to the distortion of the full arch casting. To remedy this problem an expandable container means 10 having a base means 12 with a sprue former 36 operatively disposed thereon with a full arch runner bar means 62 operatively disposed on sprue former 36 comprising a proximal end portion means 40 and distal end portion 53 with the proximal end portion means 40 forming an angle of about 55°-65° with respect to the distal end portion 53 with the distal end portion 53 forming a first 54A and second 54B curved configuration portion which together approximates the curved configuration of the jawbone of the patient with a means for interconnecting 60, 60A or 60B, the first 54A and second 54B curved configuration portion is disclosed. The interconnecting means 60A or 60B are attached to the first 54A and second 54B curved configuration portion of distal end portions 53 at any time prior to ceramic investment.

Interconnecting means 60A shown in FIG. 12, comprises an elongate bar 64 with a first and a second end having disposed on said first and second end attachment means 66. Attachment means 66 comprise a ring with an inside circumference substantially equal to the circumference of the distal end portion means 53 in order to be slidably received thereon. Interconnecting means 60B shown in FIG. 13 comprises an attachable elongate bar which is attached between, in order to interconnect, the first 54A and second 54B curved configuration portion of distal end portion 53 by a chemical adhesive such as a cyanoacrylate ester.

The preferred position of attachment of interconnecting means of 60, 60A or 60B is at an equal distance from midpoint 56 to an attachment point 68 on distal end portion 53, to form substantially equivalent angles D. Interconnecting means 60A or 60B may optionally be prepared from a pre-cast alloy, such as a nickel-chromium-beryllium alloy, or cast during the casting process within the investment container.

Figure 14:
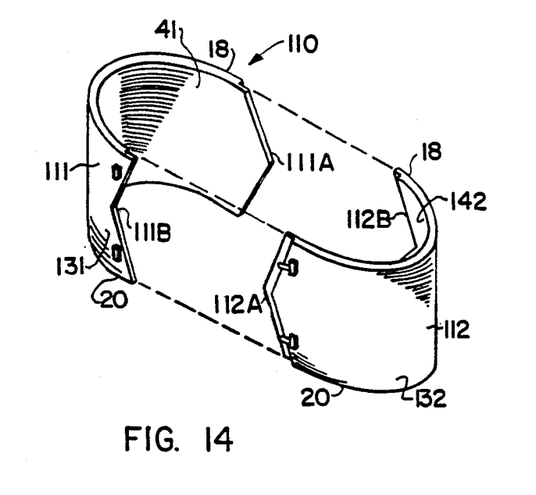
FIG. 14 is an isometric view of a second embodiment of an improved container means of the present invention.

FIG. 14 illustrates an improved the container means 110 having a first and a second open end 20 and 18 respectively. The container means 110 comprises a first and second container portion 111 and 112. The first container portion 111 has a first and a second terminating edge 111A and 111B whereas the second container portion 112 has a first and a second terminating edge 112A and 112B. The interconnection of the first and second terminating edges 111A, 111B and 112A, 112B of the first and second container portions 111 and 112 retain the uncured exothermic investment material within the container means 110 as heretofore described and as shown more fully in FIG. 15. Preferably, the first and second terminating edges 111A, 111B and 112A, 112B extend generally normal to the top surface 30 of the base means 12 as shown in FIG. 16. In the preferred embodiment, the first and second terminating edges 111A, 111B and 112A, 112B have at least a portion thereof extending angularly relative to the normal to the top surface 30 of the base means 12. This enables the stress of the expansion of the exothermic investment material to be dispersed over a wider angular surface area relative to an axis of symmetry extending through the center of the substantially cylindrical container as shown in FIG. 15.

In this embodiment, the first and second container portions 111 and 112 are identical with the second container portion 112 being inverted relative to the first container portion 111. This enables the first terminating edge 111A of the first container portion to mate with the second terminating edge 112B of the second container portion 112. Similarly, the second terminating edge 111B of the first container portion 111 matingly engages with the first terminating edge 112A of the second container portion 112. In this embodiment, the first terminating edges 111A and 112A are undercut on outer surfaces 131 and 132 of the first and second container portions 111 and 112 respectively. The second terminating edges 111B and 112B are undercut on inner surfaces 141 and 142 of the first and second container portions 111 and 112. Although the first and second terminating edges have been disclosed as being undercut, various other arrangements may be resorted to for providing cooperation between the terminating edges of the first and second container portions 111 and 112 for retaining the uncured exothermic within the container means 110.

Figure 15:
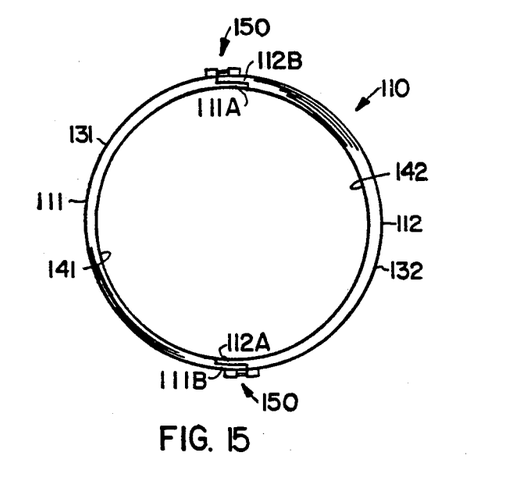
FIG. 15 is a plan view of the container means shown in FIG. 14.
Figure 16:
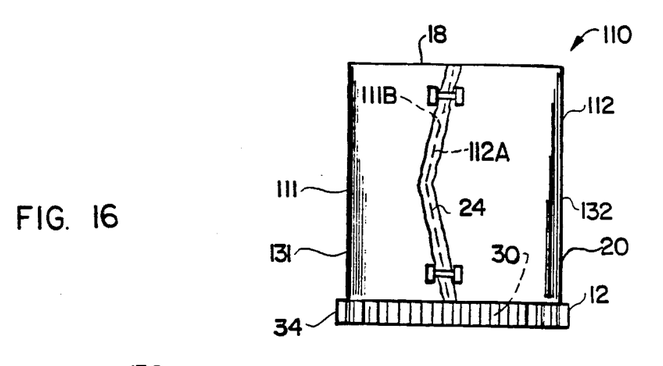
FIG. 16 is a side elevational view of the container means shown in FIG. 14 disposed on the base means.
Figure 17:
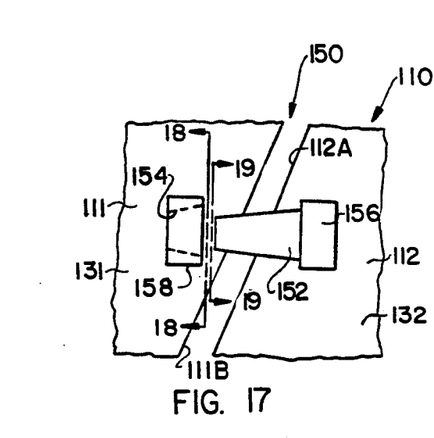
FIG. 17 is an enlarged view of a portion of FIG. 16 illustrating retaining means of the improved container means.
Figure 18:
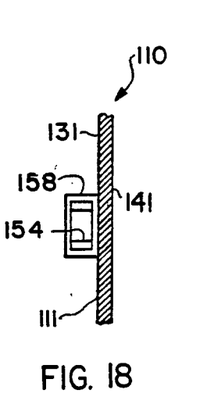
FIG. 18 is a sectional view along line 18—18 of FIG. 17.
Figure 19:
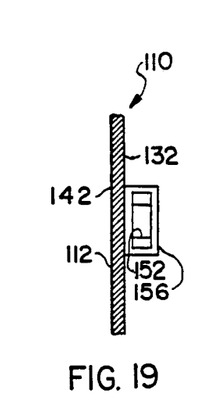
FIG. 19 is a sectional view along line 19—19 of FIG. 17.

The improved container means 110 also comprises securing means 150 shown in FIG. 15 for releasably securing first container portion 111 to the second container portion 112. FIG. 17 illustrates in greater detail the securing means 150 as comprising a tab 152 secured to the first edge 112A of the second container portion 112 and an aperture 154 disposed adjacent the second edge 111B of the first container portion 111. The tab 152 as shown is integrally formed with a boss 156 which is likewise integrally attached to the second container portion 112. The aperture 154 is defined within a boss 158 which is also integrally formed with the first container portion 111. The tab 152 is preferably tapered for facilitating the insertion of the tab 152 within the aperture 154. Likewise, the aperture 154 is similarly tapered for enabling an accurate positioning between the first and second container portions 111 and 112. Furthermore, the mating taper of the tab 152 and the aperture 154 provides a frictional engagement therebetween.

Figure 20:
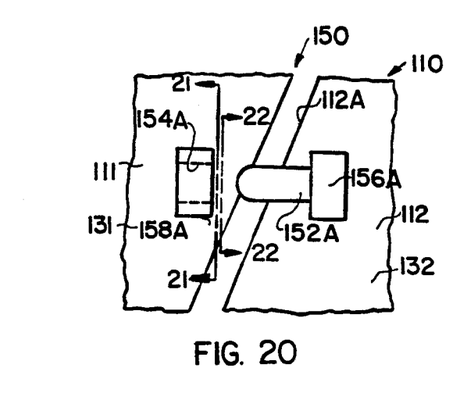
FIG. 20 is an enlarged view illustrating a second retaining means for the improved container means.
Figure 21:
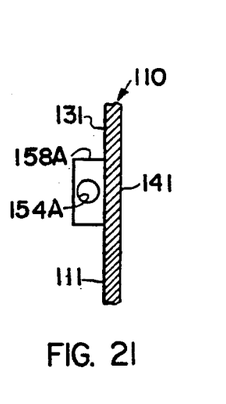
FIG. 21 is a sectional view along line 21—21 of FIG. 20.
Figure 22:
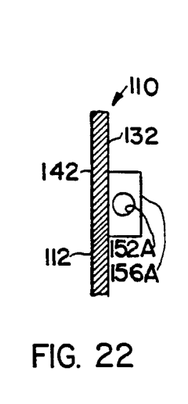
FIG. 22 is a sectional view along line 22—22 of FIG. 20.

FIGS. 20-22 illustrate a second embodiment of securing means 150A for releasably securing first container portion 111 to the second container portion 112. The securing means 150A comprises a tab 152A secured to the first edge 112A of the second container portion 112 and an aperture 154A disposed adjacent the second edge 111B of the first container portion 111. The tab 152A as shown is integrally formed with a boss 156A which is likewise integrally attached to the second container portion 112. The aperture 154A is defined within a boss 158A which is also integrally formed with the first container portion 111. The tab 152A is cylindrical having a rounded tip for facilitating the insertion of the tab 152A within the aperture 154A.

The improved container means shown in FIGS. 14-22 function in a manner similar to the investment ring or container previously described. However the improved container means 110 provides superior expansion and performance over the apparatus and method shown in FIGS. 1-13. It should be clear that the first and second terminating edges 111A and 111B of the first container portion 111 separate from the second and first terminating edges 112B and 112A of the second container portion 112 during expansion of the exothermic investment material upon the exothermic reaction thereof. In addition, as previously described, the wax 24 as shown in FIG. 16 will melt upon being heating by the exothermic reaction of the investment material to allow the separation of the terminating edges as heretofore described.

It will be seen that the objects set forth above, among those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention, as a matter of language, might be said to fall therebetween.

Now that the invention has been described,

What is claimed is:

1. An apparatus for the preparation of a dental casting from a dental pattern supported by a sprue, the apparatus utilizing an exothermic investment material which expands upon curing and utilizing a heat sealing means comprising:

base means having a top surface for supporting the sprue and the dental pattern;

container means having a first and a second open end;

said container means and said base means partially enclosing the sprue and the dental pattern when said first open end of said container means is disposed upon said top surface of said base means;

said second end of said container means enabling the introduction of the exothermic investment material to completely encompass the sprue and the dental pattern;

said container means comprising a first and a second container portion with each of said first and second container portions having a first and a second terminating edge such that the heat sealing means allows said first and second terminating edges of said first container portion respectively cooperating with said second and first terminating edges of said second container portion to retain the exothermic investment material within said container means prior to curing and allows said first and second terminating edges of said first container portion to separate from said second and first terminating edges of said second container portion during the expansion of the exothermic investment material upon the curing of the exothermic investment material.

2. An apparatus as set forth in claim 1, wherein said first and second terminating edges of said first and second container portions extend generally normal to said top surface of said base means when said first open end of said container means is disposed upon said top surface of said base means.

3. An apparatus as set forth in claim 1, wherein said first and second terminating edges of said first and second container portions have portions thereof which extend angularly relative to a line normal to said top surface of said base means when said first open end of said container means is disposed upon said top surface of said base means.

4. An apparatus as set forth in claim 1, wherein said first and second container portions are identical and said second container portion inverted relative to said first container portion for enabling said first and second terminating edges of said first container portion to respectively cooperate with said second and first terminating edges of said second container portion.

5. An apparatus as set forth in claim 1, wherein said first terminating edges of said first and second container portions are undercut on an outer surface of said first and second container portions, respectively; and said second terminating edges of said first and second container portions being undercut on an inner surface of said first and second container portions, respectively.

6. An apparatus as set forth in claim 1, further including a means for releasably securing said first container portion relative to said second container portion.

7. An apparatus as set forth in claim 6, wherein said means for releasably securing said first container portion relative to said second container portion includes a tab secured adjacent to said first edge of said second container portion; and an aperture disposed adjacent said second edge of said first container portion for receiving said tab within said aperture.

8. An apparatus as set forth in claim 1, including a tab secured adjacent to one of said first and second edges of each of said first and second container portions;

an aperture disposed adjacent to the other of said first and second edges of each of said first and second container portions; and said tabs being receivable within said apertures for releasably securing said first container portion relative to said second container portion.

9. An apparatus as set forth in claim 8, wherein each of said tabs are tapered for facilitating insertion into each of said apertures.

10. An apparatus as set forth in claim 8, wherein each of said tabs are tapered for facilitating insertion into each of said apertures; and each of said apertures being internally tapered for insuring proper alignment between said first and second container portions.

11. An apparatus as set forth in claim 1, wherein said base means includes a retaining lip extending from said top surface of said base means; and said first open end of said container means being receivable within said retaining lip of said base means for closing said first end of said container means.

12. An apparatus as set forth in claim 1, wherein said base means includes a substantially circular lip having an inside diameter extending from said top surface of said base means; and said container means being a substantially columnar tube having an outside diameter which is less than the inside diameter of said circular lip of said base means for enabling insertion of said first open end of said container means within said inside diameter of said circular lip.

13. An apparatus for the preparation of a dental casting from a dental pattern supported by a sprue, the apparatus utilizing an exothermic investment material which expands upon curing and utilizing a heat sealing means comprising:

a base means defining a top surface with a retaining lip extending from said top surface of said base means;

said base means having sprue receiving means for operatively supporting the sprue and the dental pattern from said base means;

container means having a first and a second open end;

said first open end of said container means being receivable within said retaining lip of said base means for closing said first end of said container means when said first open end of said container means is supported by said top surface of said base means;

said container means and said base means partially enclosing the sprue and the dental pattern when said first open end of said container means is closed by said top surface of said base means;

said second open end of said container means enabling the introduction of the exothermic investment material therethrough to completely encompass the sprue and the dental pattern;

said container means comprising a first and a second container portion with each of said first and second container portions having a first and a second terminating edge such that the heat sealing means allows said first and second terminating edges of said first container portion respectively cooperating with said second and first terminating edges of said second container portion for providing an engagement to retain the exothermic investment material within said container means prior to curing and allows said first and second terminating edges of said first container portion to separate from said second and first terminating edges of said second container portion upon the expansion of the exothermic investment material due to the curing of the exothermic investment material; and means for releasably securing said first container portion relative to said second container portion.

14. An apparatus as set forth in claim 13, wherein said first and second terminating edges of said first and second container portions extend generally normal to said top surface of said base means when said first open end of said container means is disposed upon said top surface of said base means.

15. An apparatus as set forth in claim 13, wherein said first and second terminating edges of said first and second container portions have portions thereof which extend angularly relative to a line normal to said top surface of said base means when said first open end of said container means is disposed upon said top surface of said base means.

16. An apparatus as set forth in claim 13, wherein said first and second container portions are identical and said second container portion is inverted relative to said first container portion for enabling said first and second terminating edges of said first container portion to respectively cooperate with said second and first terminating edges of said second container portion.

17. An apparatus as set forth in claim 13, wherein said first terminating edges of said first and second container portions are undercut on an outer surface of said first and second container portions, respectively; and said second terminating edges of said first and second container portions being undercut on an inner surface of said first and second container portions, respectively.

18. An apparatus as set forth in claim 13, wherein said means for releasably securing said first container portion relative to said second container portion includes a tab secured adjacent to said first edge of said second container portion; and an aperture disposed adjacent said second edge of said first container portion for receiving said tab within said aperture.

19. An apparatus as set forth in claim 13, wherein said means for releasably securing said first container portion relative to said second container portion includes a tab secured adjacent to one of said first and second edges of each of said first and second container portions;

an aperture disposed adjacent to the other of said first and second edges of each of said first and second container portions; and said tabs being receivable within said apertures for releasably securing said first container portion relative to said second container portion.

20. An apparatus as set forth in claim 19, wherein each of said tabs are tapered for facilitating insertion into each of said apertures.

21. An apparatus as set forth in claim 19, wherein each of said tabs are tapered for facilitating insertion into each of said apertures; and each of said apertures being internally tapered for insuring proper alignment between said first and second container portions.

22. An apparatus as set forth in claim 13, wherein said retaining lip of said base means includes a substantially circular lip having an inside diameter; and said container means being a substantially columnar tube having an outside diameter which is less than the inside diameter of said circular lip of said base means for enabling an insertion of said first open end of said container means within said inside diameter of said circular lip.

23. An apparatus for the preparation of a dental casting from a dental pattern supported by a sprue utilizing an exothermic investment material which expands upon curing comprising:

base means having a top surface for supporting the sprue and the dental pattern;

container means having a first and a second open end;

said container means and said base means partially enclosing the sprue and the dental pattern when said first open end of said container means is disposed upon said top surface of said base means;

said second end of said container means enabling the introduction of the exothermic investment material to completely encompass the sprue and the dental pattern;

said container means comprising a first and a second container portion with each of said first and second container portions having a first and a second terminating edge;

said first and second terminating edges of said first container portion respectively cooperating with said second and first terminating edges of said second container portion;

heat sealing means interconnecting said first and second terminating edges of said first and second container portions which retain the exothermic investment material within said container means prior to curing and permitting said first and second terminating edges of said first container portion to separate from said second and first terminating edges of said second container portion during the expansion of the exothermic investment material upon the curing of the exothermic investment material.

* * * * *